United States Patent [19]

Thompson

[11] Patent Number: 4,522,071

[45] Date of Patent: Jun. 11, 1985

[54] METHOD AND APPARATUS FOR MEASURING STRESS

[75] Inventor: R. Bruce Thompson, Ames, Iowa

[73] Assignee: The United States of America as represented by the United States Department of Energy, Washington, D.C.

[21] Appl. No.: 518,243

[22] Filed: Jul. 28, 1983

[51] Int. Cl.³ .............................................. G01N 29/00
[52] U.S. Cl. ......................................... 73/597; 73/643
[58] Field of Search .................................... 73/597, 643

[56] References Cited

U.S. PATENT DOCUMENTS

| 4,080,836 | 3/1978 | Thompson et al. | 73/597 |
| 4,127,035 | 11/1978 | Vasile | 73/643 |
| 4,218,924 | 8/1980 | Fortunko | 73/643 |

OTHER PUBLICATIONS

"Periodic Magnet Non-Contact Electromagnetic Acoustic Wave Transducer-Theory and Application", Vasile et al., *1977 Ultrasonics Symposium Proceedings*, IEEE Cat. #78CH1344-ISU.

Primary Examiner—Howard A. Birmiel
Attorney, Agent, or Firm—James W. Weinberger; Walter L. Rees; Judson R. Hightower

[57] ABSTRACT

A method and apparatus for determining stress in a material independent of micro-structural variations and anisotropies. The method comprises comparing the velocities of two horizontally polarized and horizontally propagating ultrasonic shear waves with interchanged directions of propagation and polarization. The apparatus for carrying out the method comprises periodic permanent magnet-electromagnetic acoustic transducers for generating and detecting the shear waves and means for determining the wave velocities.

12 Claims, 6 Drawing Figures

METHOD AND APPARATUS FOR MEASURING STRESS

CONTRACTUAL ORIGIN OF THE INVENTION

The U.S. Government has rights in this invention pursuant to Contract No. W-7405-ENG-82 between the U.S. Department of Energy and Iowa State University.

BACKGROUND OF THE INVENTION

This invention relates to a method and apparatus for measuring stress in an object. More particularly, this invention relates to a method and apparatus for measuring stress in an object by non-destructive means using ultrasonic waves.

Stress measurements are useful in determining the structural integrity and safe service life of manufactured articles. If a particular article still has useful life, it would be desirable to evaluate its stress by non-destructive means.

Several non-destructive stress evaluation techniques are known. One well-developed technique involves X-ray diffraction, in which X-rays are used to measure the distance between planes of atoms in the material being evaluated. Displacement of the planes from their normal position indicates the presence of stress in the material. Application of this method is limited by the inability of X-rays to probe deeper than about a thousand atomic layers into the material, and by the method's total inapplicability to non-crystalline materials.

Other methods of determining stress involve ultrasonic waves. All ultrasonic methods depend in principle upon the fact that the velocity of propagation of ultrasonic wave in a solid medium is influenced by stresses present in the medium. Although the effect is small, its detection and measurement are within the present state of the ultrasonic art. However, the velocity of ultrasonic waves is also affected by microstructural variations and anisotropies. Therefore, the determination of the velocity of a single ultrasonic wave alone cannot give an accurate indication of stress in a material.

It would thus be desirable to be able to measure stress in a material by ultrasonic means independent of anisotropies and microstructural variations. A theoretical basis for such measurements has been developed in the literature. In a rigorous theoretical investigation of the influence of initial stress on elastic ultrasonic waves, it was noted that the propagation of elastic waves in a material under initial stress is fundamentally different from the stress-free case, and follows laws which cannot be explained by elastic anisotropy or changes in elastic constants. Biot, Jr., Maurice A., Applied Physics, 11, 522 (1940). It has also been noted that an ultrasonic shear wave propagates faster in the direction of tension than in the perpendicular direction, analogous to a wave in a stretched string, and that the difference in $\rho V^2$ for the two waves is equal to the tensile stress, where $\rho$ is the material density and V is shear wave velocity. Thuston, R. N., J. Acoustical Society of America, 37, 348 (1965). It has been suggested that the effects of stress and texture can be separated by comparing ultrasonic wave velocities, MacDonald, Douglas E., IEEE Transactions on Sonics and Ultrasonics, SU-28 75 (1981). despite this extensive theoretical development, there has heretofore been no method or apparatus by which to apply this theory to actual stress measurements.

Previously known ultrasonic techniques have involved the use of vertically polarized or vertically propagated shear waves. For example, in the method known as shear wave birefringence, two shear waves are generated which are propagated in the same vertical direction but whose directions of polarization are orthogonal to one another. The difference in velocity between the two waves is an indication of the stress in the material. The birefringence technique is nevertheless subject to inaccuracies due to velocity shifts caused by preferred orientation of elastically anisotropic grains.

Another known method of stress measurement is set forth in U.S. Pat. No. 4,080,836 to Thompson, et al. In this method, an electromagnetic acoustic transducer generates vertically propagating orthogonally polarized shear waves in a material. The difference in velocity between the polarized waves is measured and compared to a known correlation between the difference in velocity of orthogonally polarized shear waves in the type material being measured and stress in the material. In this way the stress in the particular article is obtained. However the utility of this method is inherently limited by the accuracy of the known correlation.

SUMMARY OF THE INVENTION

It is thus one object of the invention to provide a method and apparatus for determining stress in a material.

It is another object of the invention to provide a method and apparatus for determining stress in a material independent of material anisotropies or microstructure.

It is still another object of the invention to provide a method and apparatus for determining stress in a material by non-destructive means.

Additional objects, advantages and novel features of the invention will be set forth in the following description.

According to the invention, a method and apparatus are provided for determining the stress in a material by means of ultrasonic shear waves. An electromagnetic acoustic transducer generates a first shear wave through a material, said shear wave having a known direction of propagation parallel to the surface of the material and being horizontally polarized in a direction orthogonal to the direction of propagation. A second electromagnetic acoustic transducer similar to the first transducer and positioned a known distance therefrom on the same material surface detects said shear wave, whereby the velocity of said wave is then electronically determined. By similar means, a second shear wave is generated parallel to the material surface having directions of propagation and polarization interchanged with those of said first wave. By this it is meant that the second shear wave is propagated in the direction of polarization of the first shear wave, and is polarized in the direction of propagation of the first shear wave. The second shear wave is detected and its velocity measured by similar means. The stress is then determined by comparing the velocities of said first and second shear waves. If the stress is uniaxial than the absolute stress will be measured. The determination of stress by the inventive method is independent of microstructural variations and anisotropies in the material. The inventive apparatus comprises the electromagnetic acoustic transducers configured to generate and detect the shear waves as described, and the means for measuring the shear wave velocities.

DETAILED DESCRIPTION OF THE INVENTION

The following is a description of a preferred embodiment of the invention. Other embodiments will be readily apparent to those skilled in the art.

Throughout the specification, it will be understood that "horizontal" refers to a direction parallel to the surface of an object, and "vertical" refers to a direction perpendicular to the surface of an object, regardless of the orientation of the object.

Figure 1:
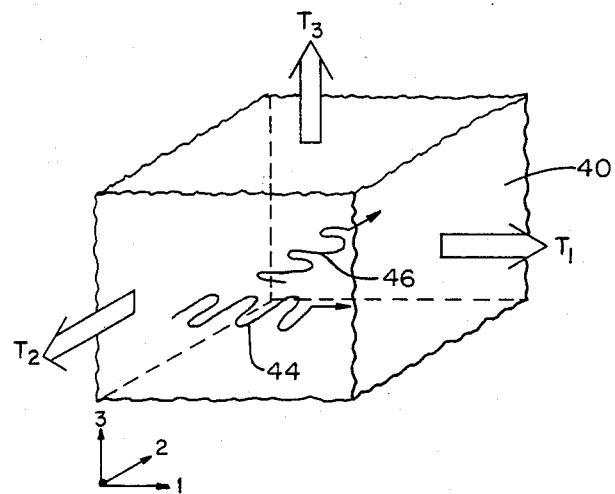
FIG. 1 illustrates the directions of propagation and polarization of the two horizontally polarized shear waves which are measured in the instant invention.

The instant invention relates to a method and apparatus for determining stress in an article by comparing the velocities of two horizontally polarized ultrasonic shear waves propagating through the article. FIG. 1 illustrates the two horizontally polarized shear waves the velocities of which are compared in accordance with the method of the instant invention. An anisotropic continuum 40 of density $\rho$ is subject to a triaxial load with stress components $T_1$, $T_2$ and $T_3$ along the three axes of the continuum. Continuum 40 is of sufficient symmetry such that the 1-axis and the 2-axis each define a pure mode direction. A pure mode direction is defined as a direction of wave propagation in which the three wave polarizations are either parallel or perpendicular to the direction of propagation. It is known, for example, that orthorhombic symmetry meets these requirements. Shear wave 44 is propagated along the 1-axis, polarized along the 2-axis, and has a velocity $V_{12}$. Shear wave 46 is propagated along the 2-axis, polarized along the 1-axis and has a velocity $V_{21}$. Both shear waves propagate in a pure mode direction. If the principle axes of stress correspond with the symmetry axes of the orthorhombic continuum the difference in stress components $T_1-T_2$ can be determined from the equation $$\rho(V_{12}^2 - V_{21}^2) = T_1 - T_2 \quad (1)$$

This is the relation derived by R. N. Thurston, cited supra.

This relation may be written as $$\rho(V_{12} - V_{21})(V_{12} + V_{21}) = T_1 - T_2 \quad (2)$$

However, it is known that the difference between the two velocities will be very small, so that $V_{12} \cong V_{21}$. Then an approximation can be made that $$\rho(V_{12} - V_{21})2\overline{V} = T_1 - T_2 \quad (3)$$

where $\overline{V}$ is an average wave velocity. Dividing both sides of this equation by $\overline{V}^2$ yields $$\frac{\rho(V_{12} - V_{21})}{\overline{V}} = \frac{T_1 - T_2}{2\overline{V}^2} \quad (4)$$

It is further known that $$\overline{V}^2 = \mu/\rho \quad (5)$$

where $\mu$ is the shear modulus. Substituting equation (5) into equation (4) gives the relation $$\frac{V_{12} - V_{21}}{\overline{V}} = \frac{T_1 - T_2}{2\mu} \quad (6)$$

This equation may then be used with experimentally determined values of $V_{12}$ and $V_{21}$ to determine the stress, $T_1-T_2$. If the stress is uniaxial along the 1-axis, then the absolute stress of the material will be determined.

The relation given applies to rolled plates as well as to a continuum as long as horizontally polarized shear waves of mode n=0 are used, because the fields of this mode coincide identically with those of a plane wave in an infinite medium. The applicability of this relation to finite plates as well as an infinite continuum was heretofore unknown and unobvious. It may be seen that the given relation between the magnitude of the velocities and the stress present in the material is independent of any proportionality constants which strongly depend on particular material properties such as microstructural variations and anisotropies. The only material constant which must be known is shear modulus, which is insensitive to microstructure, as opposed to the structurally sensitive acoustoelastic constants. The method may therefore be used with any object which meets the aforementioned symmetry requirements, whether the material is polycrystalline, a single crystal, a ceramic, or other type of material.

It may be seen that the instant invention requires a means of generating and detecting horizontally polarized pure mode shear waves. If the object whose stress is to be measured is an electrically conductive material such as a metal, then it is preferred that the waves be generated and detected by means of periodic permanent magnet electromagnetic acoustic tranducers, known in the art as PPM-EMAT's.

PPM-EMAT's generally comprise a plurality of permanent magnets arranged such that the polarity alternates, thereby establishing a periodic magnetic bias field. The magnets are wound with a coil such that when the transducer is placed near a metal object and current is caused to flow through the coil, the transducer will induce eddy currents to flow through the metal such that the $\vec{J} \times \vec{B}$ Lorentz force is parallel to the metal surface and perpendicular to the winding direction. The resulting force excites only horizontally polarized waves in a plate. Alternatively, eddy currents flowing through the plate will induce a current to flow through the coil of a transducer placed near the plate. Hence, the transducer so configured can detect as well as generate shear waves. Prior art PPM-EMAT's are described in detail in Vasile, C. F. and Thompson, R. B., J. Applied Physics, 50, 2583 (1979).

Figure 2:
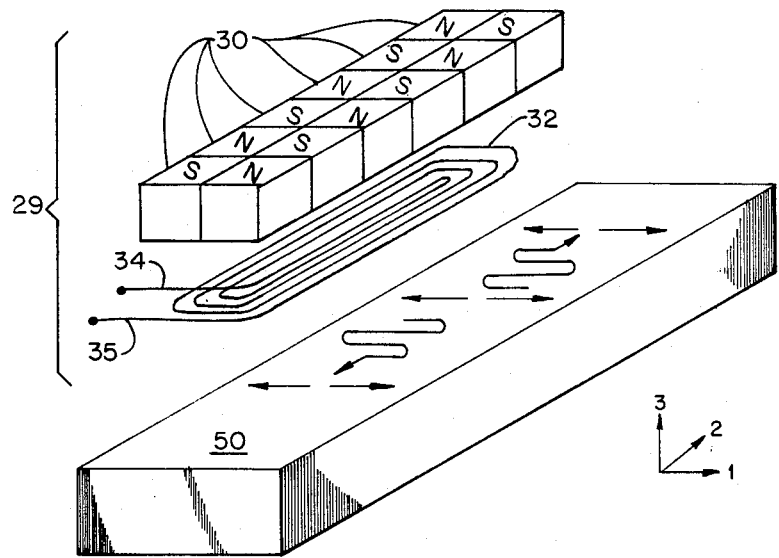
FIG. 2 illustrates an electromagnetic acoustic transducer of the type used in the instant invention.

FIG. 2 is an exploded view of a preferred configuration of a PPM-EMAT 29 for use in the instant invention. Permanent magnets 30 are arranged so that the polarity alternates. Mounted directly below the magnets is elongated spiral coil 32 through which electrical current is circulated. Coil 32 is provided with leads 34 and 35 for connecting the PPM-EMAT to the associated electronics. The PPM-EMAT is shown relative to a plate 50 experiencing stress along the 1-axis. In this configuration and orientation the PPM-EMAT radiates horizontally polarized shear waves propagating along the 2-axis. It should be noted that although plate 50 may experience stress along the 3-axis, that stress will be equal to zero at the surface of the plate and will not distort the velocity determination.

Figure 3:
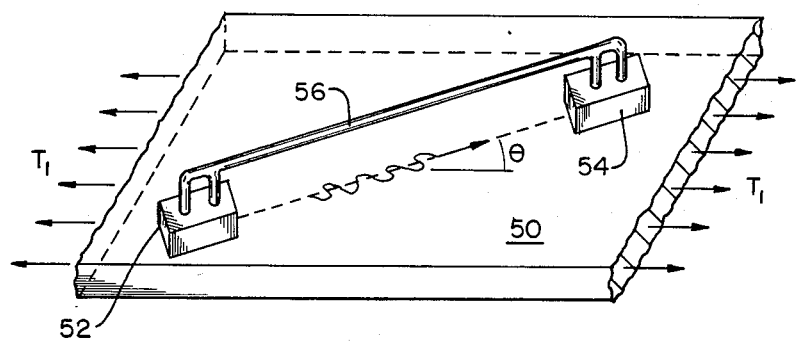
FIG. 3 illustrates an embodiment of the inventive apparatus.

FIG. 3 illustrates a possible configuration of the inventive apparatus. Two PPM-EMAT's 52 and 54 are shown positioned on a surface of a textured metal plate 50 which is subject to a uniform uniaxial stress in the direction $T_1$ as indicated by the arrows. The PPM-EMAT's 52 and 54 are separated by spacer bar 56 of known length. The PPM-EMAT's are generally oriented along the principal stress axes of the plate 50 corresponding to $\theta=0$ and $\theta=90°$ C. As previously described, the principal stress axes corresponds to the symmetry axes of the plate. One PPM-EMAT will be pre-set to transmit an ultrasonic shear wave propagating along the line between the PPM-EMAT's, and the other PPM-EMAT will be pre-set to receive the wave.

According to the method of the invention, the apparatus is positioned on the surface of rolled plate 50, a horizontally polarized shear wave of mode $n=0$ is generated in the pate and its velocity is measured. The apparatus is then repositioned to generate a second horizontally polarized shear wave propagated in a direction perpendicular to the direction of propagation of the first wave. The velocity of this wave is also measured. The magnitudes of the shear wave velocities are then compared according to the equation (6) set forth above to determine the stress of the plate.

Figure 4:
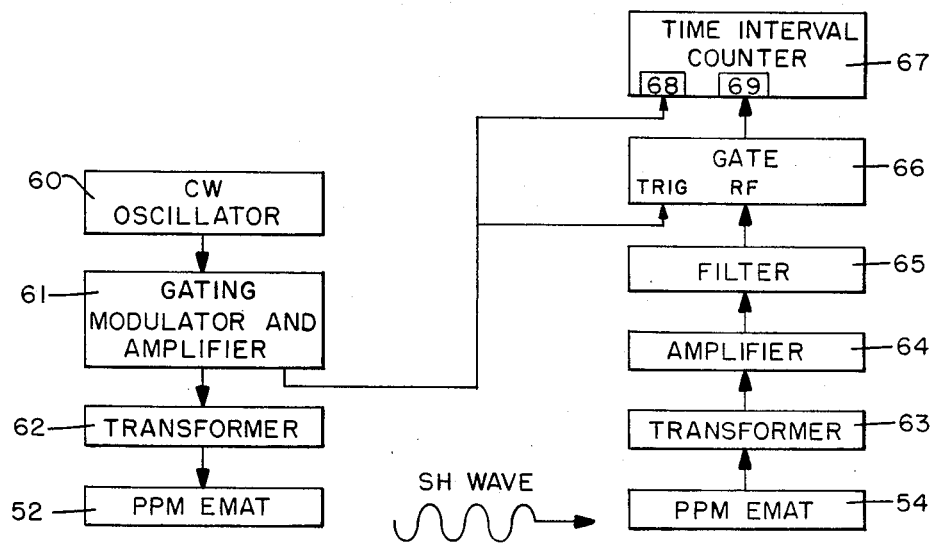
FIG. 4 is a schematic diagram of the electronic circuitry used to measure the velocities of the shear waves.

The electronic system for measuring the velocities of the shear waves is illustrated schematically in FIG. 4. Continuous wave oscillator 60 generates a signal which is transmitted through gating modulator and amplifier 61, which changes the continuous wave signal to pulses of several cycles. The pulsed signal is transmitted to the "start" trigger 68 of time interval counter 67. The signal is also transmitted through transformer 62 to the first PPM-EMAT 52 which generates a shear wave. The shear wave propagates through the material undergoing evaluation, whereby its velocity is shifted by the stress of the material. The shifted shear wave is detected by second PPM-EMAT 54 which responds by generating a signal. This signal is transmitted through transformer 63, amplifier 64, filter 65, and gate 66 to "stop" trigger 69 of time interval counter 67.

Time interval counter 67 measures the time between the excitation of PPM-EMAT 52 and the arrival of the shear wave at PPM-EMAT 54. Start trigger 68 and stop trigger 69 respond when the voltages they experience first cross an instrumentally determined threshold with a specified slope. While the start signal is derived from the gating modulator pulse, the signal from filter 65 cannot be used as a stop signal because the leakage from the start signal would exceed the threshold before the shear wave reached PPM-EMAT 54. Gate 66 eliminates the leakage, and also eliminates the leading part of the shear wave signal so that the cleanest possible trigger signal is derived. This gate is synchronized to the excitation of the ultrasonic wave by the start trigger pulse provided by the gating modulator. Thus, while each velocity measurement will include an extra delay factor, this extra delay factor will be the same for each shear wave. Then when two velocities are compared according to equation (6) the delay factors will exactly cancel each other out.

Figure 5:
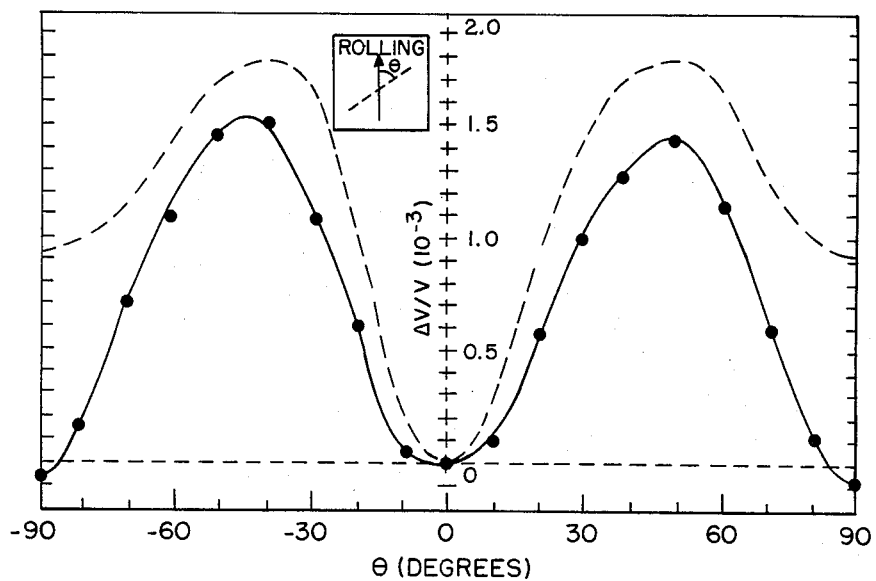
FIG. 5 illustrates the results of wave velocity measurements made on an unstressed plate, and illustrates the anticipated results of wave velocity measurements made on a stressed plate.

FIG. 5 illustrates the results of wave velocity measurements taken on an unstressed rolled plate of 6061 aluminum of approximate dimensions $2' \times 2' \times 1/16''$. The horizontal axis indicates in degrees the angle $\theta$, which is the angle between the direction of rolling and the direction of wave propagation. The vertical axis indicates the difference in velocities between the measured wave and the wave which propagates in the direction of rolling. As shown by the solid curve, the difference in velocities varies with the angle of measurement in an unstressed plate. The variation indicates the presence of anistropies and microstructural texture in the plate. However, in the special cases when $\theta=0$ and $\theta=90$, the velocities of the two waves are about the same, indicating that the relative values of these two the wave velocities are independent of anistropies and microstructures.

The dashed curve in FIG. 5 illustrates the anticipated results of the same measurements performed on a rolled plate subject to an uniaxial stress in the direction of rolling. In this case, the velocities of the two waves are not the same. The difference is due entirely to the applied stress and is determinative of the stress of the material independent of anistropies and microstructures.

Figure 6:
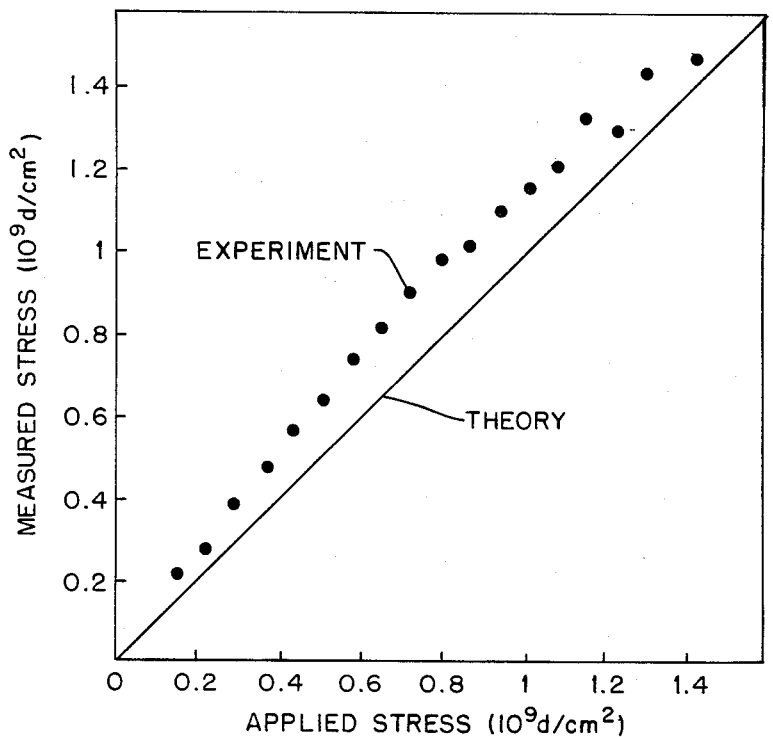
FIG. 6 illustrates the results of stress measurements made on a stressed plate with the method and apparatus of the instant invention.

FIG. 6 shows the results of stress measurements made with the method and apparatus of the instant invention. A second rolled aluminum plate, cut from the same aluminum piece as the plate used in the experiments in FIG. 5, was subjected to applied stresses by known experimental means. According to theory, the measured stress as shown by the dots should be identical to the applied stress as shown by the solid line. The experimental data are seen to be in good agreement with the theory.

The foregoing is a description of a preferred embodiment of the instant invention. Other embodiments will be apparent to those skilled in the art. For example, the invention may be used on a curved surface as well as a flat surface if known correction factors are used in determining the velocities of the generated shear waves. In addition, electronic means may be used to store and compare the measured velocities of the shear waves. The embodiment described herein is not intended to limit the invention to the precise form disclosed, but was chosen in order to best explain the principles of the invention and its practical application.

The embodiments of this invention in which an exclusive property or privilege is claimed are defined as follows:

1. A method of determining stress in an object comprising:
   generating a first horizontally polarized ultrasonic shear wave through said object, said first wave having a known direction of propagation parallel to the surface of said object,
   determining the velocity of said first wave,
   generating a second horizontally polarized ultrasonic shear wave through said object, the direction of propagation and polarization of said second wave being interchanged with those of said first wave, determining the velocity of said second wave, and determining the stress in said object according to the formula:

$$\rho(V_{12}^2 - V_{21}^2) = T_1 - T_2$$

where
$V_{12}$ = the velocity of said first wave
$V_{21}$ = the velocity of said second wave
$\rho$ = the density of the material, and
$T_1 - T_2$ = the stress of the material.

2. The method of claim 1 wherein said horizontally polarized shear waves are generated by means of a first periodic permanent magnet electromagnetic acoustic transducer (PPM-EMAT).

3. The method of claim 2 wherein the velocity of each shear wave is determined by detecting said shear wave by means of a second periodic permanent magnet electromagnetic acoustic transducer positioned a known distance from said first PPM-EMAT and determining the elapsed time between wave generation and wave detection.

4. The method of claim 1 wherein said object is of orthorhombic symmetry.

5. The method of claim 4 wherein said object is a flat plate.

6. The method of claim 4 wherein said stress is uniaxial such that the absolute stress of the object is determined.

7. A method of determining stress in an object comprising:
generating a first horizontally polarized ultrasonic shear wave through said object, said first wave having a known direction of propagation parallel to the surface of said object,
determining the velocity of said first wave,
generating a second horizontally polarized ultrasonic shear wave through said object, the direction of propagation and polarization of said second wave being interchanged with those of said first wave,
determining the velocity of said second wave, and
determining the stress in said object according to the formula:

$$\frac{V_{12} - V_{21}}{V} = \frac{T_1 - T_2}{2\mu}$$

where
$V_{12}$ = the velocity of said first wave
$V_{21}$ = the velocity of said second wave
$V$ = an average wave velocity
$T_1 - T_2$ = the stress of the material, and
$\mu$ = the shear modulus of the material.

8. The method of claim 7 wherein said horizontally polarized shear waves are generated by means of a first periodic permanent magnet electrochemical acoustic transducer (PPM-EMAT).

9. The method of claim 8 wherein the velocity of each shear wave is determined by detecting said shear wave by means of a second periodic permanent magnet electromagnetic acoustic transducer positioned a known distance from said first PPM-EMAT and determining the elapsed time between wave generation and wave detection.

10. The method of claim 7 wherein said object is of orthorhombic symmetry.

11. The method of claim 10 wherein said object is a flat plate.

12. The method of claim 10 wherein said stress is uniaxial such that the absolute stress of the object is determined.

* * * * *